US010722192B2

(12) United States Patent
Erler et al.

(10) Patent No.: US 10,722,192 B2
(45) Date of Patent: Jul. 28, 2020

(54) VARIABLE STOP APPARATUS AND COMPUTED-TOMOGRAPHY SCANNER COMPRISING A VARIABLE STOP APPARATUS

(71) Applicant: Carl Zeiss Industrielle Messtechnik GmbH, Oberkochen (DE)

(72) Inventors: Marco Erler, Oberkochen (DE); Daniel Weiss, Essingen-Forst (DE); Wolfgang Kimmig, Aalen (DE); Martin Krenkel, Aalen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 9 days.

(21) Appl. No.: 16/258,262

(22) Filed: Jan. 25, 2019

(65) Prior Publication Data
US 2019/0231286 A1 Aug. 1, 2019

(30) Foreign Application Priority Data
Jan. 26, 2018 (DE) .......................... 10 2018 201 250

(51) Int. Cl.
| A61B 6/00 | (2006.01) |
| A61B 6/03 | (2006.01) |
| G01N 23/046 | (2018.01) |
| H05G 1/02 | (2006.01) |
| A61B 6/06 | (2006.01) |
| G21K 1/04 | (2006.01) |

(52) U.S. Cl.
CPC ............ *A61B 6/4028* (2013.01); *A61B 6/032* (2013.01); *A61B 6/06* (2013.01); *A61B 6/4064* (2013.01); *G01N 23/046* (2013.01); *G21K 1/04* (2013.01); *H05G 1/02* (2013.01); *G01N 2223/419* (2013.01)

(58) Field of Classification Search
CPC .................................. A61B 6/032; A61B 6/06
See application file for complete search history.

(56) References Cited

U.S. PATENT DOCUMENTS

| 3,869,615 | A | | 3/1975 | Hoover et al. | |
| 5,359,639 | A | * | 10/1994 | Saito | ...................... A61B 6/032 378/4 |
| 7,831,023 | B2 | * | 11/2010 | Wedel | ...................... A61B 6/06 378/148 |

(Continued)

FOREIGN PATENT DOCUMENTS

| DE | 3246114 A1 | 6/1984 |
| DE | 69301692 T2 | 7/1996 |

(Continued)

*Primary Examiner* — Dani Fox
(74) *Attorney, Agent, or Firm* — Falk Ewers; Ewers IP Law PLLC (57) ABSTRACT

A variable stop apparatus for arrangement between an X-ray source and an object to be measured in a CT-scanner and a CT-scanner including the variable stop apparatus are provided. The variable stop apparatus includes a stop carrier that is pivotable about a pivot axis. The stop carrier has at least two stops. The at least two stops are in each case configured to be brought into a predetermined angular position by pivoting the stop carrier. The at least two stops are arranged at different longitudinal positions with respect to a longitudinal direction that is defined by the pivot axis.

9 Claims, 4 Drawing Sheets

(56) References Cited

U.S. PATENT DOCUMENTS 9,250,432 B2    2/2016   Weiss et al.
9,279,776 B2    3/2016   Kleine et al.

FOREIGN PATENT DOCUMENTS

| | | |
|---|---|---|
| DE | 102007019334 A1 | 11/2008 |
| DE | 102010042351 A1 | 4/2012 |
| DE | 102012208710 B3 | 9/2013 |

* cited by examiner

VARIABLE STOP APPARATUS AND COMPUTED-TOMOGRAPHY SCANNER COMPRISING A VARIABLE STOP APPARATUS

CROSS REFERENCE TO RELATED APPLICATIONS

This application claims priority to German patent application DE 10 2018 201 250.4, filed on Jan. 26, 2018, the entire content of which is incorporated herein by reference.

TECHNICAL FIELD

The invention relates to a variable stop apparatus and to a Computed-Tomography (CT) scanner comprising the variable stop apparatus.

BACKGROUND

When measuring objects using computed tomography, scattered radiation is undesirable, because it increases the signal background and noise of the detector signals and furthermore produces undesired artefacts in the reconstructed images. The scattered radiation can be reduced if the computed tomography system is designed and/or operated such that only a limited, relevant solid angle range is illuminated with X-rays. If only relevant object details are irradiated, that is to say only those parts of which the image information is actually used, the image quality can be improved.

In microfocus sources which are also operated at high power and therefore with focal spot sizes up to the millimeter range, the used ray angle is generally so large that only part of the X-ray beam is incident on the sensor surface of the detector and another part travels past the sensor surface or is incident next to the sensor surface. The reason for this is that the sensor surface would otherwise be illuminated inhomogeneously. In order to obtain sufficiently homogeneous illumination, it is typical to select used ray angles that are of a size such that the sensor surface is illuminated many times over. In a computed tomography system having a variable distance between X-ray source and detector, the used ray angle should, with a constant size of the sensor surface, be adapted to the distance to reduce scattered radiation.

In this respect, two procedures are known from the related art. In the first procedure, a stop size, i.e., an aperture of the stop, which defines the used ray angle is selected to have a size such that the sensor surface of the detector is completely illuminated even in the case of the largest possible focal spot. The stop is here located at a fixed distance from the focal spot, independently of the size of the focal spot.

The second procedure provides a window collimator, which is adjustable by a motor and which permits the setting of the size of the illuminated region in one or two direction(s) that extend transversely to the propagation direction of the radiation. The stop windows of the collimator are located in a common plane at a distance from the focal spot which is not adaptable to a change in the focal spot size. The sharpness of the imaging of the stop windows in the detector plane therefore depends on the stop size.

Also known from medical technology, in which the radiation exposure of a patient is to be kept as small as possible, are so-called "multi-leaf" collimators. The latter consist of leaves that are adapted for individual recordings to the recording conditions. However, for automated actuation, a great number of independent actuators are used.

SUMMARY

It is an object of the invention to provide a variable stop apparatus and a CT-scanner with which scattered radiation can be reduced.

The object is achieved by a variable stop apparatus and by a CT-scanner as disclosed herein.

The invention is based on the finding that a stop size, i.e., an aperture of the stop, which is optimal with respect to a detector surface to be illuminated, and an optimum distance of the stop from the focal spot of the X-ray source exist for a focal spot size which is specified by specified measurement conditions such as, a power of the X-ray source. A larger stop should here ideally be positioned at a greater distance from the focal spot to produce a minimum unsharpness in the detector plane and to hereby in turn be able to keep the used ray angle as small as possible.

Proposed in particular is a variable stop apparatus arranged between an X-ray source and an object to be measured in a CT-scanner, having a stop carrier that is pivotable about a pivot axis, wherein the stop carrier has at least two stops, and wherein the at least two stops are in each case able to be brought into a predetermined angular position by pivoting the stop carrier, and wherein at least two of the at least two stops are arranged at different longitudinal positions with respect to a longitudinal direction that is defined by the pivot axis. Owing to the ability to bring different stops, which are additionally arranged at different longitudinal positions, into the predetermined position, the stop apparatus is variable. In particular, the at least two stops are situated permanently at the same position relative to one another with respect to the stop carrier. Therefore, by pivoting the stop carrier, all stops are shifted at the same time about the pivot axis and maintain their angle distance with respect to one another.

An arrangement of stops at different longitudinal positions with respect to a longitudinal direction that is defined by the pivot axis means in particular that the respective exit planes from which radiation exits during operation through said stops toward the detector are disposed in different planes which are transverse and in particular perpendicular to the pivot axis. In general, the exit plane of the stop is the plane that has the minimum opening cross section for the passage of radiation. If the stop has in the propagation direction of the radiation one or more longitudinal sections with an opening cross section of constant size, the exit plane is that plane which, during operation, is disposed at the greatest distance in the propagation direction of the radiation from the radiation source and thus closest to the object that is to be irradiated.

Further provided is a CT-scanner including at least one exemplary embodiment of the variable stop apparatus, wherein the at least one variable stop apparatus is arranged such that the stop that is positioned at the predetermined angular position is located in the beam path between a focal spot of an X-ray source of the CT-scanner, and an object that is to be measured. The variable stop apparatus is therefore arranged such that, during operation of the CT-scanner, invasive radiation from the X-ray source passes in particular without absorption through the respective stop that is positioned at the predetermined angular position and enters the region in which the object that is to be measured is located. The radiation proportion that is not scattered or absorbed by the object can be detected by a detector of the CT-scanner.

In particular, the pivot axis can coincide with an axis of symmetry of the, for example, conical X-ray beam or a central axis of the X-ray beam.

A fundamental idea of the invention is to arrange a plurality of stops, i.e., at least two stops, at a pivotable stop carrier. Each of the plurality of stops can be brought into a predetermined angular position by way of a pivot movement of the stop carrier about the pivot axis. At this angular position, during operation, the respective stop is located in the beam path between a radiation source and an object that is to be measured in a CT-scanner, with the result that the radiation passes through the stop at the predetermined angular position and the used ray angle (i.e., the solid angle of the usable radiation) is determined by the stop. At least two of the plurality of stops are arranged at different longitudinal positions with respect to a longitudinal direction that is defined by the pivot axis. This allows not only for a stop to be brought into the beam path in a targeted fashion by pivoting the stop carrier, but also for the longitudinal position of the stop used during operation to be set, and thereby also for a distance between the X-ray source and the respectively used stop or for a position of the stop between the focal spot of the X-ray source and the X-ray detector to be set. The stop used can therefore be positioned at a suitable distance from the focal spot of the X-ray source.

Compared to a linear movement of one of a plurality of available stops, which are connected to one another into a predetermined position, the invention has the advantage that less space is required.

In particular, the stop carrier can have a disk, for example a circular disk, in which case the stop carrier has a stop wheel, since the disk can be referred to as a wheel. Located within the disk face are the apertures, which means that an X-ray beam can pass through the disk face when the X-ray beam is directed at the aperture. The disk consists of a material that absorbs X-rays and absorbs X-rays in particular with a high absorptance, with the result that it is substantially only the X-rays that pass through the respective aperture unimpeded that reach a region in which an object that is to be measured is located.

The predetermined angular position into which the stops are able to be pivoted individually can optionally be one of a plurality of predetermined angular positions within a continuous region of angular positions. This makes it possible in particular to radiate X-rays into different partial regions in which an object that is to be investigated and measured can be situated. In other words, a specific stop can be used in different angular positions within the continuous region such that X-rays are irradiated onto the object that is to be investigated through the aperture of the stop.

In one exemplary embodiment, provision is made for the at least two stops to have different stop shapes and/or stop dimensions. The terms stop shape and stop dimension relate to the shape or dimensions of the aperture of the stop. By selecting one of a plurality of different stop shapes, it is possible to ensure that only partial regions of a detector of the CT-scanner that correspond to the stop shape are illuminated and/or partial regions of an object to be measured that correspond to the stop shape are irradiated.

The power of the X-ray source can generally be set continuously. At increased power of the X-ray source, in many cases the focal spot size of the X-ray source also increases. In accordance with the laws of geometric imaging, this focal spot size defines at a given magnification an unsharpness in the detector plane. Ideally, the unsharpness should here not be greater than a resolution of the detector, i.e., it should correspond to the size of a sensor element of the detector.

That means that for a greater radiant flux density, the distance of the stop from the X-ray source should also be greater. Therefore, a distance of the used stop from the X-ray source that is as great as possible is always desired to minimize the unsharpness or the extent of a half shadow of the stop in the detector plane and also the used ray angle of the X-rays.

In one exemplary embodiment, provision is therefore made for the longitudinal positions of the stops to be selected in dependence on a stop shape and/or on stop dimensions of the stops and/or on a focal spot size corresponding to the respective stop. With specified imaging conditions, a specified focal spot size and a specified stop shape and size, a longitudinal position of the stop can thus be selected. It is thus possible, with a given focal spot size, to select and/or set a suitable associated longitudinal position of the stop or of the stops and thus a distance between the X-ray source and the stop or a position of the stop between the focal spot of the X-ray source and the X-ray detector. In the case of a small focal spot size, the longitudinal position of the associated stop can be selected such that the distance between the X-ray source and the stop is correspondingly smaller than in the case of a large focal spot size. The longitudinal positions of the plurality of stops can be selected such that the distances required for the respectively provided focal spot sizes at which an acceptable unsharpness of the imaging is achieved are obtained.

The at least two stops used generally differ in particular in pairs with respect to the stop dimensions and the longitudinal position, or the distance of the stop from the focal spot of the X-ray source, and optionally also with respect to the stop shape. However, it is also possible for the aperture sizes and/or the longitudinal positions of two stops to be the same, while the stop shapes differ.

At least one stop, in particular having large stop dimensions (i.e., a large aperture), e.g., at a longitudinal position at a greater distance from the focal spot of the X-ray source than at least another stop of the apparatus, can be embodied in a hollow cylinder and/or tube having a radiation-absorbing wall. Thereby, the entry of scattered radiation from the outer periphery of the stop into the region of the object that is to be measured can be reduced. For this reason, provision is made in one exemplary embodiment for the stop carrier to include at least one tube, in particular a stop cylinder. This tube carries the stop. In particular, a longitudinal axis of the tube extends through the cavity of the tube, and, during operation of the stop apparatus, a stop is located within the tube at a longitudinal position with respect to the longitudinal axis that is at a distance from the object-side end of the tube. For example, the exit opening of the stop with reference to the longitudinal extent of the tube with respect to the longitudinal axis can have a distance from the object-side end that corresponds to at least a third and preferably at least half the longitudinal extent of the tube.

In particular when the stop carrier includes a disk extending in a main plane, a cross-sectional area of the cavity of the tube can be congruent with a cutout in the disk which is correspondingly provided therefor. During operation of the apparatus, the longitudinal axis of the tube extends from the X-ray source away in the direction of the object that is to be measured and the detector, with the result that the X-ray beam can pass through the stop within the tube when this stop is arranged at the predetermined angular position. The radiant flux density of scattered radiation in the region of the object that is to be examined and on the detector is then reduced by the lateral surface of the tube and by the disk.

Provision is made in one exemplary embodiment for the stop carrier to include at least two planes which are offset with respect to one another in the longitudinal direction, wherein the at least two planes extend in each case transversely to the pivot axis (in particular perpendicularly to the pivot axis and/or parallel with respect to a sensor surface of the detector), and wherein an exit opening of one of the stops is arranged in each of the planes. The planes which are offset with respect to one another can be used to ensure that the stops in the CT-scanner are located at different distances from a focal spot of an X-ray source.

Provision is made in one exemplary embodiment for the variable stop apparatus to include a motor, wherein the motor is set up to drive the stop carrier and to hereby bring in each case one of the stops into the predetermined angular position. The motor is controlled by an associated controller, for example. The controller can here be set up to bring, after receiving a control signal, a stop corresponding to the control signal into the predetermined angular position by actuating the motor.

The stop is movable into the predetermined angular position with a high degree of positioning accuracy. To this end, the motor controller can be combined with a high-resolution measurement system for measuring the position. In particular, the motor can exert a holding force that holds the stop in the predetermined angular position even in the case of expected external forces. Furthermore, the motor can be a stepper motor. The step width in this case is typically configured to have a given accuracy in the setting of the predetermined angular position.

In a further exemplary embodiment, provision is made for the variable stop apparatus to have a filter arrangement that is arranged at a distance from the stop carrier. By pivoting the filter arrangement about a pivot axis, individual filters are able to be brought into a predetermined angular position, with the result that, during operation, an X-ray beam passes through the filter in its predetermined angular position and through an aperture of the stop in its predetermined angular position. The filter arrangement can in particular be a filter wheel (more particularly arranged parallel with respect to the stop carrier). The filter arrangement and the stop carrier can typically be able to be shifted about the same pivot axis. In more general terms, the pivot axes can extend parallel with respect to one another. In any case, both a filter and a desired stop of the stop apparatus can be moved into the beam path of the X-ray beam. The properties of the used beam can hereby be improved.

In an exemplary embodiment, provision is furthermore made for a motor to be set up to drive both the stop carrier and the filter arrangement and in particular the filter wheel. Provision can be made here for example for the motor to drive only the stop carrier or the filter arrangement at a time. This can be effected for example using a correspondingly formed transmission with a clutch. It is then possible to deliberately select whether the filter arrangement or the stop carrier is to be driven. Using a single motor for both wheels, it is possible to save costs for material and installation space in the CT-scanner.

A material thickness of the material used for forming the stop should not be arbitrarily thin, but is, for example, in the millimeter range to sufficiently block the radiation. The material is typically a highly absorbing material with respect to X-rays, such as a material including tungsten or lead or combinations thereof. For this reason, provision is made in one exemplary embodiment for a thickness of the stop carrier and of the at least two stops to have a minimum value. Here, the minimum value is determined on the basis of material parameters of the materials used and is dependent on the ability of the material to block X-rays and to ensure mechanical stability. Generally, the minimum value for the thickness will be the larger the higher the required positioning accuracy is, because a greater thickness ensures better stability of the stop carrier and of the stops.

The variable stop apparatus can include further elements, such as a bearing, which supports the stop carrier, and/or a base or support, by way of which the stop carrier can be connected to a housing of the CT-scanner. The variable stop apparatus can furthermore include mechanical transmission devices such as a transmission, belts etc., which ensure that the stop carrier can be driven mechanically. In particular, a motor can drive the stop carrier via the transmission and/or a belt. For accurately determining the angular position of the stop carrier, the variable stop apparatus can furthermore have a mechanical or optical pulse generator.

BRIEF DESCRIPTION OF THE DRAWINGS

The invention will now be described with reference to the drawings wherein.

DESCRIPTION OF EXEMPLARY EMBODIMENTS

Figure 1A:
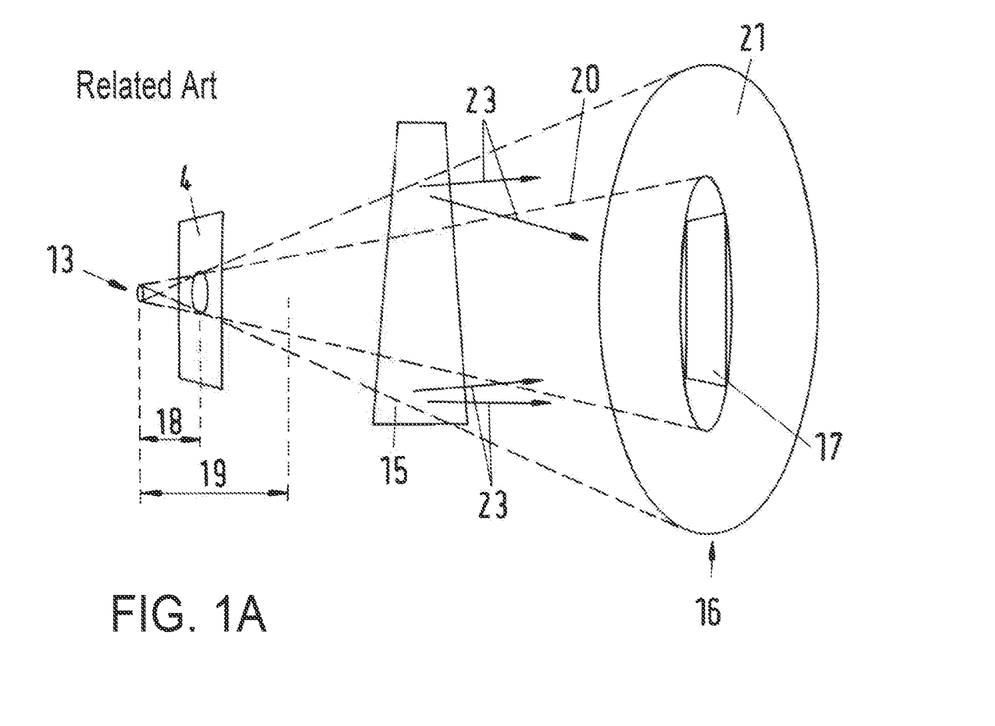
FIG. 1A shows a schematic illustration of a beam path in a CT-scanner for illustrating the generation of undesired scattered radiation in accordance with the related art.
Figure 1B:
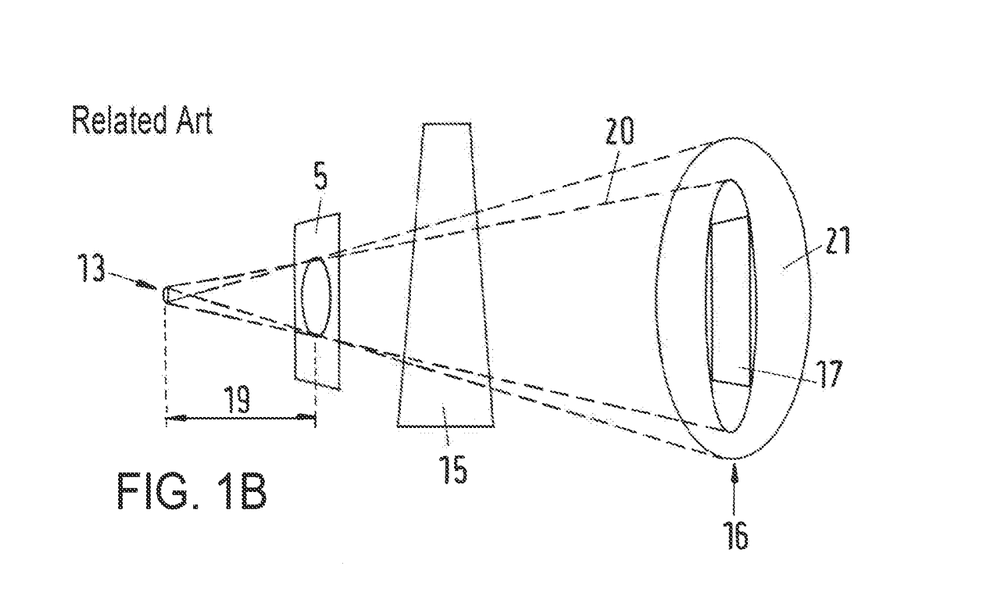
FIG. 1B shows a schematic illustration of the beam path shown in FIG. 1A, in which undesired scattered radiation is reduced on account of a deliberately selected, greater distance of the stop from the focal spot of the X-ray source, likewise in accordance with the related art.

FIG. 1A shows a beam path in a CT-scanner for illustrating the generation of occurring scattered radiation 23. Illustrated schematically in the beam path from left to right are a focal spot 13 of an X-ray source, a small stop 4, an object 15 that is to be measured, and a detector 16 having a detector surface 17. The small stop 4 is disposed at a small distance 18 from the focal spot 13. FIG. 1A also illustrates a large distance 19 from the focal spot. In the arrangement illustrated in FIG. 1B, a large stop 5 is located at this large distance 19. In particular within the beam cone of a half shadow 21 of the stop 4 in accordance with FIG. 1A, disturbing scattered radiation 23 is produced, which is incident on the detector surface 17 and there results in undesired measurement artefacts.

The size of the half shadow 21 and consequently the scattered radiation can be reduced by positioning the large stop 5, i.e., a stop having a larger aperture than the small stop 4, at the great distance 19 from the focal spot 13, which is greater than in FIG. 1A. This is shown schematically in FIG. 1B. Here, the large stop 5 is positioned at a large distance 19 from the focal spot 13 of the X-ray source. As a result, the size of the half shadow 21 decreases with the used beam 20 remaining the same. The region between the focal spot 13 and the detector 16 onto which radiation is directly incident is reduced. It is consequently also not possible in this region for any additional scattered radiation 23 to be produced which would then be partially incident on the detector 16 and would be detected by the detector 16.

Figure 2A:
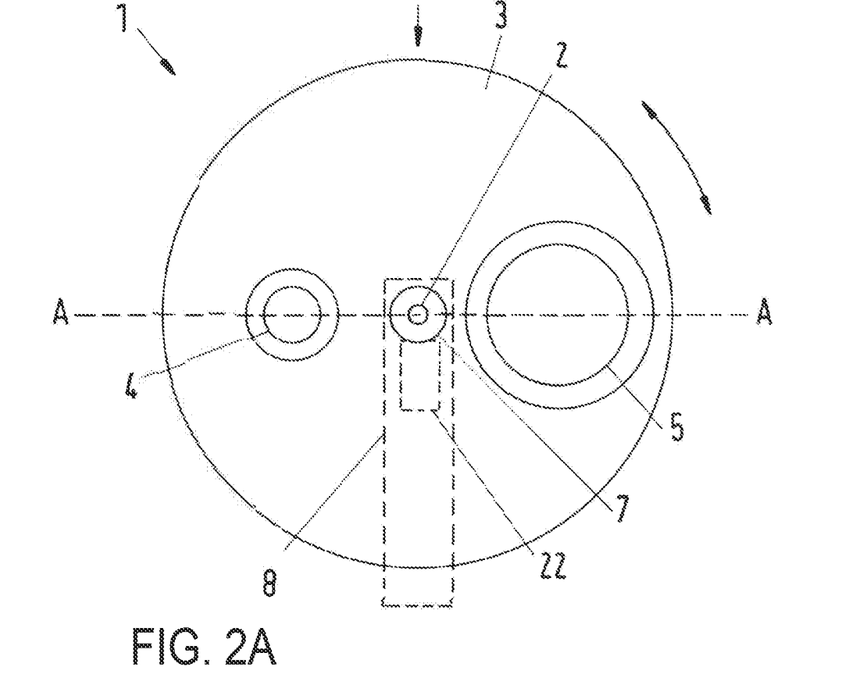
FIG. 2A shows a schematic front view of an exemplary embodiment of the variable stop apparatus.

FIG. 2A shows a schematic illustration of an exemplary embodiment of the variable stop apparatus 1. The variable stop apparatus 1 includes a stop carrier 3 which is pivotable about a pivot axis 2, and, in the exemplary embodiment, takes the shape of a stop wheel. The pivotable stop carrier 3 carries two stops 4, 5 and/or forms two stops 4, 5. The stops 4, 5 in the exemplary embodiment differ with respect to the diameter of their circularly round aperture. The small stop 4 has a small aperture, while the large stop 5 has an aperture which is larger than the stop 4.

The two stops 4, 5 can be brought individually into a predetermined angular position 6 by pivoting the stop carrier 3. The variable stop apparatus 1 is then arranged in a CT-scanner such that the pivotable stop carrier 3 and the predetermined angular position 6 are positioned and are oriented such that the stop 4, 5 which is arranged in each case at this predetermined angular position 6 is positioned in a beam path between a focal spot of an X-ray source and the object that is to be measured. Thereby, the small stop 4 or the large stop 5 can optionally be positioned in the beam path by pivoting the pivotable stop carrier 3.

The variable stop apparatus 1 can include further elements. For example, the variable stop apparatus 1 can have a bearing 7 for supporting the pivotable stop carrier 3 and a holder 8, which accommodates the bearing 7 and hereby connects the pivotable stop carrier 3 to a housing of the CT-scanner. A motor 22 arranged on the holder 8 can serve to drive the pivotable stop carrier 3 and bring one of the stops 4, 5 into the predetermined angular position 6.

Figure 2B:
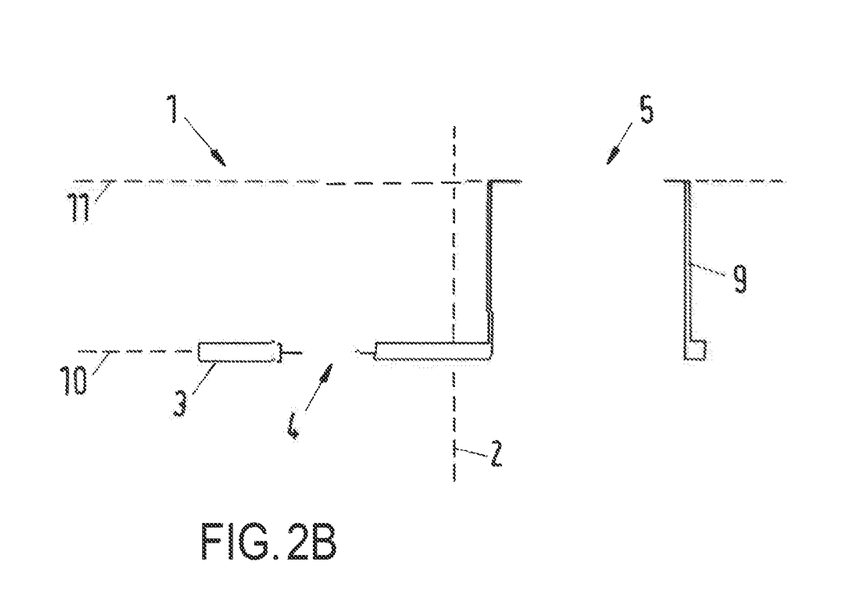
FIG. 2B shows a schematic cross-sectional illustration through the exemplary embodiment of the variable stop apparatus shown in FIG. 2A along the section line A-A.

FIG. 2B also shows the pivotable stop carrier 3. The stop 5 has a tube with an area (cross-sectional area of the cavity at the stop carrier 3) that is formed in a main plane of the stop carrier 3. The (in this case cylindrical) tube 9 forms the large stop 5, wherein an aperture of the large stop 5 is formed at a distal end of the tube 9 at the object-side end of the tube 9. The apertures of the stops 4, 5 are arranged at different longitudinal positions with respect to a longitudinal direction that is defined by the pivot axis 2, with the result that the respective exit planes from which radiation passing through said stops 4, 5 exits during operation in the direction of the X-ray detector are situated in different planes 10, 11 which are perpendicular to the pivot axis 2. The respective exit planes can thereby be positioned optimally between the focal spot of the X-ray source and the X-ray detector. A used ray profile of the X-rays can thereby be set in each case optimally for different operating conditions.

Figure 3A:
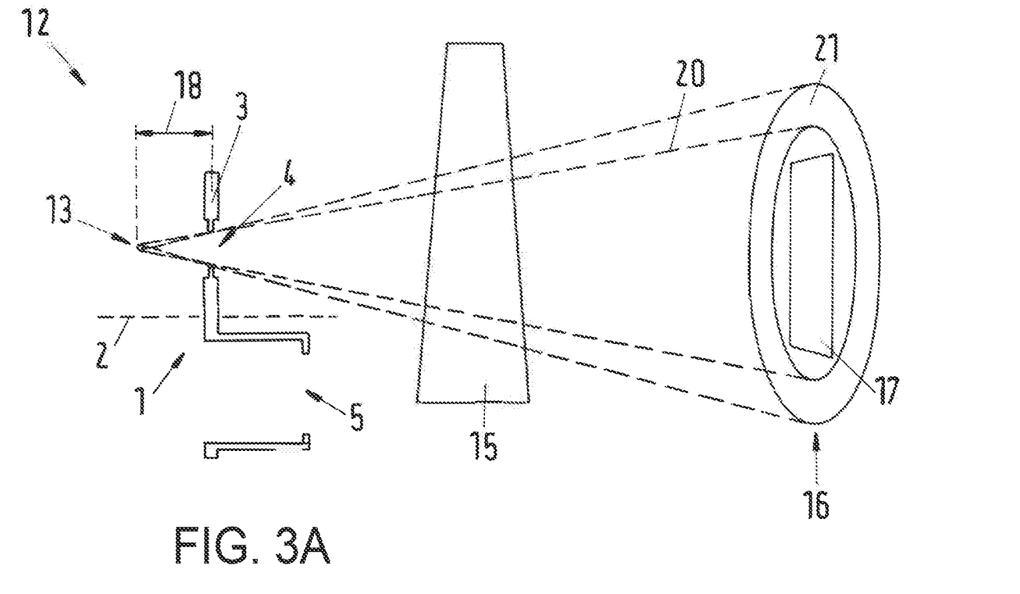
FIG. 3A shows a schematic illustration of the exemplary embodiment of the variable stop apparatus shown in FIGS. 2A and 2B in a beam path of a CT-scanner with a set small stop.
Figure 3B:
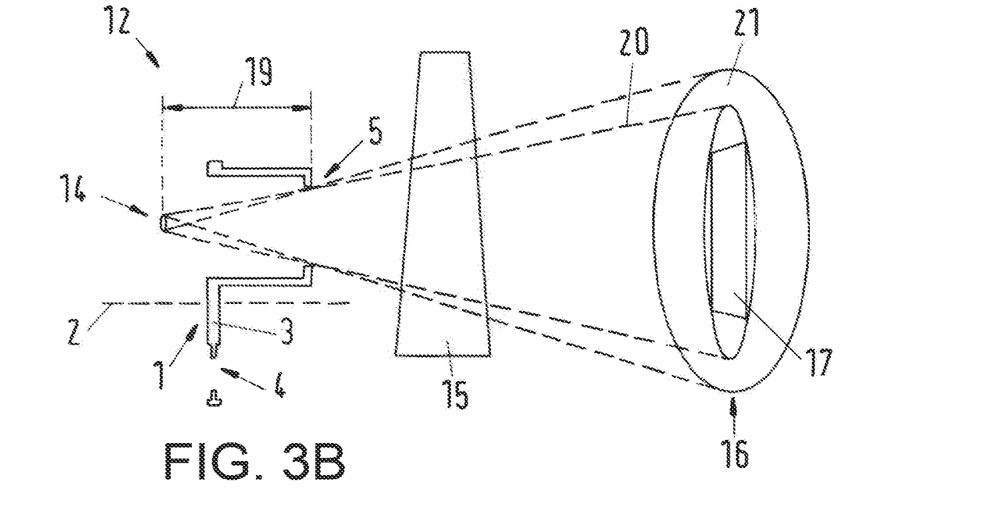
FIG. 3B shows a schematic illustration of the exemplary embodiment of the variable stop apparatus shown in FIGS. 2A and 2B in a beam path of a CT-scanner with a set large stop.

FIGS. 3A and 3B explain the function of the variable stop apparatus 1 on the basis of two schematic illustrations of the variable stop apparatus 1 arranged in the beam path of a CT-scanner 12. Illustrated schematically in the beam path from left to right are a focal spot 13, 14 of an X-ray source, the variable stop apparatus 1, an object 15 that is to be measured, and a detector 16 having a detector surface 17. The variable stop apparatus 1 corresponds to the exemplary embodiment illustrated schematically in FIGS. 2A and 2B, which is to say it has a small stop 4 having a smaller aperture and a large stop 5 with a larger aperture and also a tube 9. The variable stop apparatus 1 is arranged in the beam path of the CT-scanner such that the stop 4, 5, which is positioned at the predetermined angular position of the stop carrier 3, is situated in the beam path.

In FIG. 3A, the CT-scanner 12 is operated for example at low power of the X-ray source, that is to say with a small focal spot 13. As explained above, it is then expedient to use the small stop 4 having a small distance 18 from the focal spot 13 to optimally adapt the used ray profile. For this reason, the small stop 4 is brought into the predetermined angular position (which, in the illustration of the FIGS., is located at the uppermost vertex of the pivotable stop carrier 3) by pivoting the pivotable stop carrier 3 about the pivot axis 2. The aperture of the small stop 4 is then located in the beam path. The variable stop apparatus 1 is arranged in the beam path such, and a longitudinal position of the small stop 4 on the pivotable stop carrier 3 is such, that the small stop 4 is then positioned at a small distance 18 from the focal spot 13. At this small distance 18, the small stop 4 is positioned optimally with respect to the focal spot 13, with the result that the detector surface 17 is optimally illuminated by the used beam 20, and a half shadow 21 outside the detector surface 17 is small.

Another situation is illustrated in FIG. 3B. Here, the CT-scanner is to be operated at a larger power of the X-ray source, that is to say with a large focal spot 14. Accordingly, when the large stop 5 is used, the large distance 19 from the large stop 5 to the large focal spot 14 is larger than the small distance 18 in the situation shown in FIG. 3A. This is achieved by rotating the pivotable stop carrier 3 about its pivot axis 2 until the large stop 5, the aperture of which is formed at the distal end of the tube 9, is pivoted into the predetermined angular position in the beam path. The large stop 5 is then positioned at the large distance 19 from the focal spot 14, with the result that the detector surface 17 is optimally illuminated by the used beam 20, and a half shadow 21 outside the detector surface 17 is small.

Figure 4A:
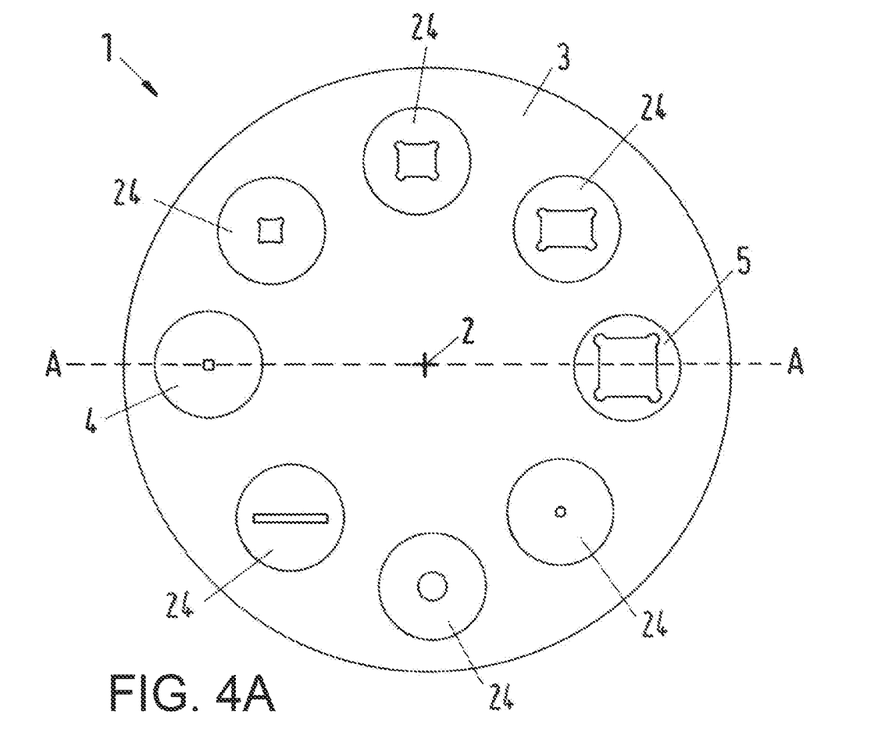
FIG. 4A shows a schematic front view of a further exemplary embodiment of the variable stop apparatus.
Figure 4B:
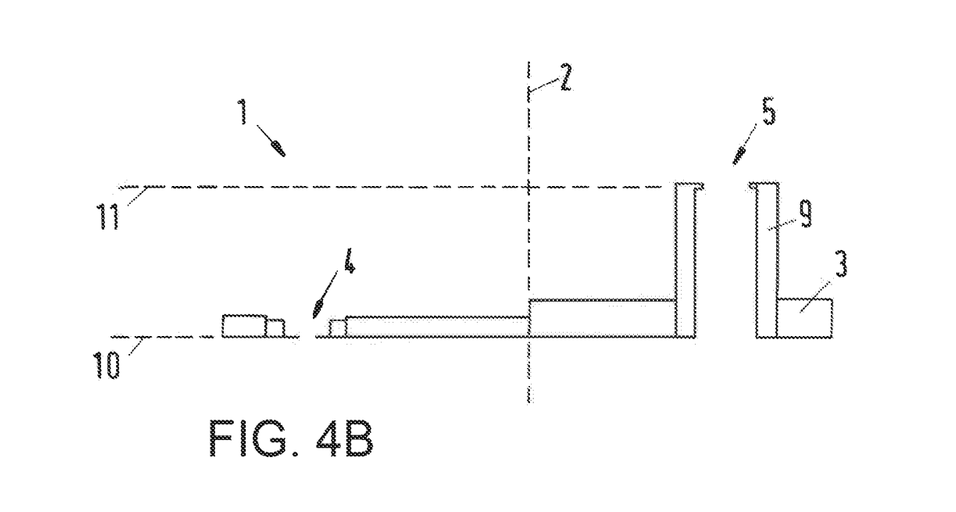
FIG. 4B shows a schematic cross-sectional illustration through the further exemplary embodiment of the variable stop apparatus shown in FIG. 4A along the section line A-A.

A further exemplary embodiment of the variable stop apparatus 1 is depicted in FIGS. 4A and 4B. The exemplary embodiment in parts of its features corresponds to the exemplary embodiment shown in FIGS. 2A and 2B, but includes a total of eight stops 4, 5, 24. Six of the stops are designated each with the reference sign 24 to indicate that the number of stops can vary. For this reason, in another exemplary embodiment, only the stops 4, 5 and one or two further stops 24 are present, for example. The stops 4, 5, 24 are typically distributed uniformly over the circumferential direction, i.e., over the angle region around the pivot axis.

Here, all stops 4, 5, 24 differ in terms of their stop shape and/or in terms of their stop dimensions, i.e., the associated apertures of the stops 4, 5, 24 differ in terms of shape and size. In this exemplary embodiment, a selection of eight different stops 4, 5, 24 can thus be provided, and by pivoting the stop carrier 3, the respectively desired stop 4, 5, 24 can be positioned at the predetermined angular position into the beam path between a X-ray source and an object.

Typically, all stops are located here at different longitudinal positions with respect to the longitudinal direction that is defined by the pivot axis 2, with the result that the respective exit planes from which radiation passing through said stops 4, 5, 24 exits during operation in the direction of the X-ray detector are located in different planes 10, 11, which are perpendicular to the pivot axis 2 (FIG. 4B only shows the planes 10, 11 for the stops 4, 5). The longitudinal positions here are in each case selected such that the stops 4, 5, 24 are located at a desired distance or at a distance that corresponds to a focal spot size and stop size from the focal spot of the X-ray source (cf. FIG. 3A and FIG. 3B). Such a variable stop apparatus 1 has the advantage that a plurality of different stops 4, 5, 24 can be positioned flexibly at different distances from the focal spot or at different positions between the focal spot and the X-ray detector in the beam path.

It is understood that the foregoing description is that of the exemplary embodiments of the invention and that various changes and modifications may be made thereto without departing from the spirit and scope of the invention as defined in the appended claims.

LIST OF REFERENCE NUMERALS

1 Variable stop apparatus
2 Pivot axis
3 Stop carrier
4 Stop
5 Stop
6 Predetermined angular position
7 Bearing
8 Holder
9 Tube
10 Plane
11 Plane
12 CT-scanner
13 Focal spot
14 Focal spot
15 Object
16 Detector
17 Detector surface
18 Small distance
19 Large distance
20 Used beam
21 Half shadow
22 Motor
23 Scattered radiation
24 Further stop

What is claimed is:

1. A variable stop apparatus for arrangement between an X-ray source and an object to be measured in a Computed-Tomography (CT) scanner, the variable stop apparatus comprising:
a stop carrier including at least two stops and being pivotable about a pivot axis;
each of the at least two stops being configured to be individually brought into a predetermined angular position by pivoting the stop carrier; and
at least two of the at least two stops being arranged at different longitudinal positions in a longitudinal direction defined by the pivot axis.

2. The variable stop apparatus as claimed in claim 1, wherein the at least two stops have at least one of different stop shapes or stop dimensions, respectively.

3. The variable stop apparatus as claimed in claim 1, wherein the different longitudinal positions are selected depending on at least one of a stop shape, a stop dimension, and a focal spot size.

4. The variable stop apparatus as claimed in claim 1, wherein:
the stop carrier includes at least one tube, and
one of the at least two stops is arranged in a cavity of the at least one tube.

5. The variable stop apparatus as claimed in claim 1, wherein:
the stop carrier includes at least two planes which are offset with respect to one another in the longitudinal direction,
each of the at least two planes extends in a direction transverse to the pivot axis, and
each of the at least two planes defines an exit opening of one of the at least two stops, respectively.

6. The variable stop apparatus as claimed in claim 1, further comprising:
a motor configured to drive the stop carrier and to thereby bring one of the at least two stops into the predetermined angular position.

7. The variable stop apparatus as claimed in claim 6, further comprising:
a filter arrangement arranged at a distance from the stop carrier and configured to bring individual filters into the predetermined angular position by pivoting the filter arrangement about the pivot axis to permit an X-ray beam to pass through a filter in its predetermined angular position and through an aperture of a stop of the at least two stops in its predetermined angular position during operation.

8. The variable stop apparatus as claimed in claim 7, wherein the motor is configured to drive both the stop carrier and the filter arrangement.

9. A CT-scanner comprising:
the variable stop apparatus as claimed in claim 1, the variable stop apparatus being arranged to permit the at least two stops positioned at the predetermined angular position to be located in the beam path between a focal spot of the X-ray source of the CT-scanner and the object to be measured.

* * * * *